US009260751B2

(12) United States Patent
Diehl et al.

(10) Patent No.: US 9,260,751 B2
(45) Date of Patent: Feb. 16, 2016

(54) SINGLE-MOLECULE PCR ON MICROPARTICLES IN WATER-IN-OIL EMULSIONS

(71) Applicant: The Johns Hopkins University, Baltimore, MD (US)

(72) Inventors: Frank Diehl, Schortens (DE); Kenneth W. Kinzler, Baltimore, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/261,837

(22) Filed: Apr. 25, 2014

(65) Prior Publication Data

US 2015/0119287 A1    Apr. 30, 2015

Related U.S. Application Data

(62) Division of application No. 12/305,825, filed as application No. PCT/US2007/014273 on Jun. 19, 2007, now Pat. No. 8,715,934.

(60) Provisional application No. 60/814,585, filed on Jun. 19, 2006.

(51) Int. Cl.
*C12Q 1/68*    (2006.01)

(52) U.S. Cl.
CPC .............. *C12Q 1/686* (2013.01); *C12Q 1/6876* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2004/0106120 A1 | 6/2004 | Tazi-Ahnini et al. |
| 2005/0064460 A1 | 3/2005 | Holliger et al. |
| 2005/0227264 A1 | 10/2005 | Nobile et al. |
| 2006/0025363 A1 | 2/2006 | Breitenbach et al. |
| 2006/0040297 A1 | 2/2006 | Leamon et al. |
| 2006/0068390 A1 | 3/2006 | Tillett et al. |

FOREIGN PATENT DOCUMENTS

| | | |
|---|---|---|
| WO | 01/95934 | 12/2001 |
| WO | WO 02/22869 | 3/2002 |

OTHER PUBLICATIONS

Archer et al., Eng. Chem. Prod. Res. Dev., vol. 16, pp. 319-325, 1977.
M.A. Mays, Pure & Appl. Chem., vol. 61, pp. 1373-1378, 1989.
UOP960-06 Trace Oxygenated Hydrocarbons in Liquid Hydrocarbon Streams by GC. [retrieved on Jan. 10, 2013]. Retrieved from the internet: <http://www.astm.org/Standards?UOP960.htm>.
Stan et al. (Anal. Chem., vol. 81, pp. 2399-2402 and Supplemental Information; 2009).
The definition of "mineral oil" provided by the website dictionary. com [retrieved on Oct. 12, 2012], retrieved from the internet: <URL:dictionary.reference.com/browse/mineral+oil.>.

(Continued)

*Primary Examiner* — Robert T Crow
(74) *Attorney, Agent, or Firm* — Banner & Witcoff, Ltd.

(57) ABSTRACT

Modulation of the viscosity of the oil phase of a microemulsion used for amplification of DNA on a bead increases the homogeneity of product beads and the amount of amplified DNA per bead. Moreover the number of separate microemulsion populations that can be formed in parallel is increased using multi-well plates and mixer mill disrupter machines designed to lyse biological samples.

12 Claims, 3 Drawing Sheets

(56) References Cited

OTHER PUBLICATIONS

The product data sheet provided by carechemicals [retrieved on May 14, 2012], retrieved from the internet: <URL:www.cospha.ro/dbimg/Cetiol%20A.pdf>.

Whitesides et al., Anal. Chem. vol. 81, pp. 2399-2402 and Supplemental Information, 2009.

Supplemental European Search Report in Application No. 07809665.8 dated Jun. 9, 2010.

Dressman et al., "Transforming single DNA molecules into fluorescent Magnetic Particles for Detection and Enumeration of Genetic Variations," Proceedings of the National Academy of Sciences of the United States, vol. 100, No. 5, Jul. 22, 2003, pp. 8817-8822.

Musyanovych et al., "Miniemulsion droplets as single molecule nanoreactors for polymerase chain reaction," Biomacromolecules, vol. 6, No. 4, Jul. 2005, pp. 1824-1828.

Anonymous "TissueLyser System" Jan. 1, 2004, Retrieved from the internet URL:http://www.saimd.com/sqlimages/QIAGEN/1025397.pdf.

M.J. Brisco et al., "Detection and Quantification of Neoplastic Cells in Acute Lymphoblastic Leukaemia, by Use of the Polymerase Chain Reaction," British Journal of Haematology, 1991, 79, 211-217.

M.J. Brisco et al., "Outcome Prediction in Childhood Acute Lymphoblastic Leukaemia by Molecular Quantification of Residual Disease at the End of Induction," The Lancet, Jan. 22, 1994, vol. 343, pp. 196-200.

P.J. Sykes et al., "Quantification of Targets for PCR by Use of Limiting Dilution," BioTechniques, 1992, vol. 13, No. 3, pp. 444-449.

Diehl et al. Beaming: single-molecule PCR on microparticles in water-in-oil emulsions. Nature Methods 3(7):551-559 Jul. 2006, published online Jun. 21, 2006. See entire article, especially p. 554 steps 9-13.

Park et al. Rheological properties and stabilization of magnetorheological fluids in a water-in-oil emulsion. Journal of Colloid and Interface Science 240:349-354 (2001). See entire article, especially p. 350, first paragraph under "A. Material Preparation".

TEGOSOFT DEC product information sheet [online] May 2003 [retrieved on Jul. 17, 2008] retrieved from: http://www.frankenchemie.de/img/DS_TEGOSOFT_DEC_e.pdf.

Diehl et al. Detection and quantification of mutations in the plasma of patients with colorectal tumors. Proceedings of the National Academy of Sciences, USA 102(45):16368-16373, Nov. 8, 2005. See entire article, especially p. 16369, p. 16369, "Beaming".

Pandolfe et al. Effect of dispersed and continuous phase viscosity on droplet size of emulsions generated by homogenization. J. Dispersion Science and Technology 2(4):459-474 (1981). See entire article.

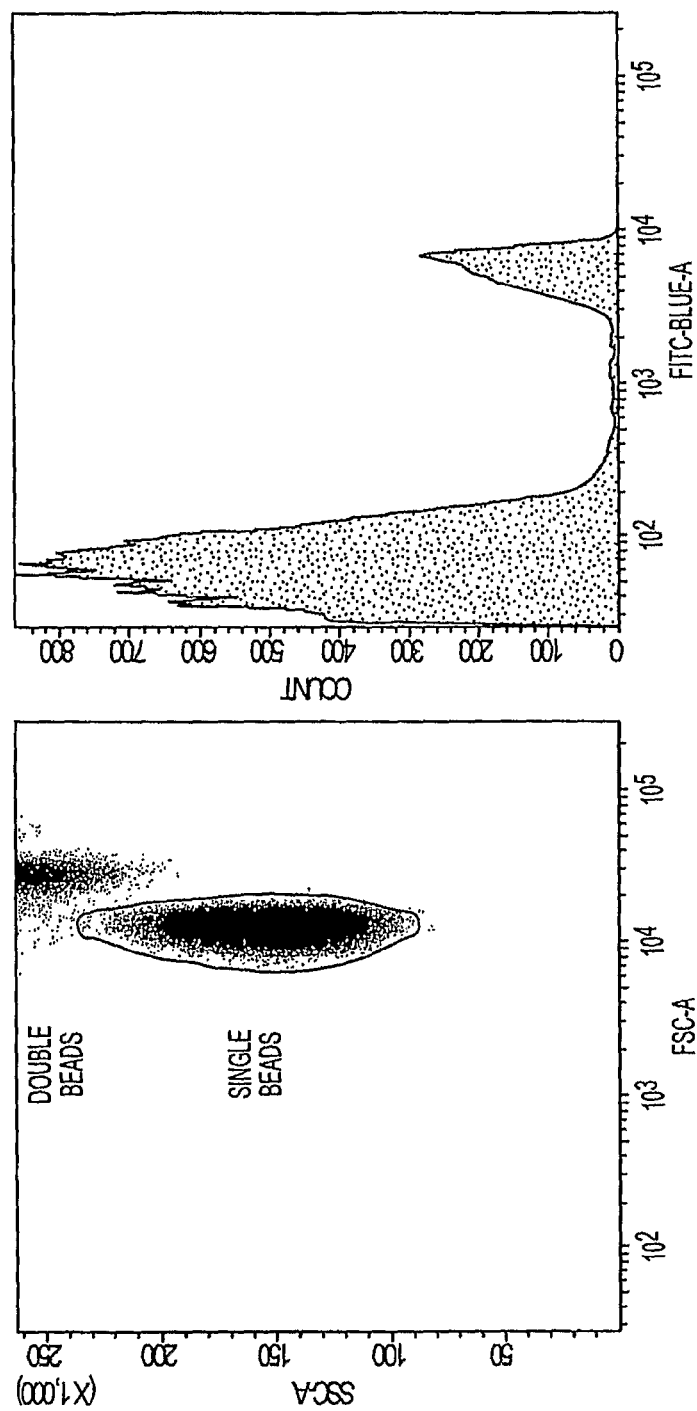

SEQUENCE LISTING

```
<160> NUMBER OF SEQ ID NOS: 3

<210> SEQ ID NO 1
<211> LENGTH: 20
<212> TYPE: DNA
<213> ORGANISM: Homo sapiens

<400> SEQUENCE: 1
tcccgcgaaa ttaatacgac                                              20

<210> SEQ ID NO 2
<211> LENGTH: 18
<212> TYPE: DNA
<213> ORGANISM: Homo sapiens

<400> SEQUENCE: 2
gctggagctc tgcagcta                                                18

<210> SEQ ID NO 3
```

```
<211> LENGTH: 21
<212> TYPE: DNA
<213> ORGANISM: Homo sapiens

<400> SEQUENCE: 3
ttcccgcgaa attaatacga c                                      21
```

SINGLE-MOLECULE PCR ON MICROPARTICLES IN WATER-IN-OIL EMULSIONS

The U.S. government retains certain rights in the invention by virtue of grants from the NIH including CA 43460, CA57345, and CA 62924.

The entire disclosure of U.S. provisional application Ser. No. 60/814,585 filed Jun. 19, 2006, is expressly incorporated herein.

TECHNICAL FIELD OF THE INVENTION

This invention is related to the area of DNA analysis. In particular, it relates to the amplification and segregation of single species of DNA molecules.

BACKGROUND OF THE INVENTION

The most important biotechnological advances made in the $20^{th}$ century involved methods that convert a single DNA molecule into a population of identical DNA molecules. The first wave of techniques for this purpose employed cells (cloning) and the second wave employed PCR. Cloning was advantageous in that the populations emanating from individual molecules were inherently separated through this process. In contrast, PCR-based methods required individual compartments (tubes) for each template if the products were to be kept separate. Emulsion PCR overcame this disadvantage by miniaturizing the compartments so that millions of templates could be individually amplified within a single tube.

BEAMing (beads, emulsions, amplification, and magnetics) built on emulsion PCR by keeping products formed within each compartment together once the emulsions were broken. This was accomplished through (i) inclusion of beads within the compartments and (ii) ensuring that one strand of the PCR product is bound to the beads. After amplification, each bead is coated with thousands of copies of the single DNA molecule present in the compartment that contained that bead and these beads could easily be recovered with a magnet or by centrifugation.

Beads obtained via BEAMing accurately reflect the DNA diversity present in the template population and can be used to determine what fraction of a DNA population contains a specific mutation. Because each bead contains thousands of molecules of the identical sequence, the signal to noise ratio obtained with hybridization or enzymatic assays is extremely high. Millions of beads can be analyzed within minutes using conventional flow cytometry or optical scanning instruments. The DNA bound to the beads also provides excellent templates for high-throughput sequencing.

There is a continuing need in the art to improve the throughput of DNA amplification to improve analysis of DNA and genetic diagnoses.

SUMMARY OF THE INVENTION

According to one embodiment of the invention a method for analyzing nucleotide sequence variations is provided. Microemulsions comprising an oil phase and an aqueous phase are formed. The aqueous phase comprises one or more species of analyte DNA molecules. From 10-30% (v/v) of the microemulsions is the aqueous phase and from 70-90% (v/v) of the microemulsions is the oil phase. The oil phase comprises one or more low viscosity hydrocarbons with a viscosity less than 20 mPas at 25° C. in an amount from 60-85% (v/v) of the oil phase, one or more high viscosity hydrocarbons having a viscosity of greater than 20 mPas at 25° C. in an amount from 10-30% (v/v), and an emulsifier in an amount from 5-10% (v/v). Analyte DNA molecules in the microemulsions are amplified in the presence of reagent beads. The reagent beads are bound to a plurality of molecules of a primer for amplifying the analyte DNA molecules. Product beads are formed which are bound to a plurality of copies of one species of analyte DNA molecule. The product beads are separated from analyte DNA molecules which are not bound to product beads. A sequence feature of the one species of analyte DNA molecule which is bound to the product beads is determined.

A liquid composition is provided by the present invention. It comprises a plurality of microemulsions forming aqueous compartments wherein at least a portion of said aqueous compartments comprise a bead, a polynucleotide template, and oligonucleotide primers for amplifying said template. At least a portion of the oligonucleotide primers is bound to the bead. The microemulsions comprise an oil phase and an aqueous phase. From 10-30% (v/v) of the microemulsions is the aqueous phase and from 70-90% (v/v) of the microemulsions is the oil phase. The oil phase comprises one or more low viscosity hydrocarbons with a viscosity less than 20 mPas at 25° C. in an amount from 60-85% (v/v) of the oil phase, one or more high viscosity hydrocarbons having a viscosity of greater than 20 mPas at 25° C. in an amount from 10-30% (v/v), and an emulsifier in an amount from 5-10% (v/v).

Another embodiment of the invention is a method for isolating nucleotide sequence variants. Microemulsions comprising an oil phase and an aqueous phase are formed. The aqueous phase comprises one or more species of analyte DNA molecules. From 10-30% (v/v) of the microemulsions is the aqueous phase and from 70-90% (v/v) of the microemulsions is the oil phase. The oil phase comprises one or more low viscosity hydrocarbons with a viscosity less than 20 mPas at 25° C. in an amount from 60-85% (v/v) of the oil phase, one or more high viscosity hydrocarbons having a viscosity of greater than 20 mPas at 25° C. in an amount from 10-30% (v/v), and an emulsifier in an amount from 5-10% (v/v). Analyte DNA molecules in the microemulsions are amplified in the presence of reagent beads. The reagent beads are bound to a plurality of molecules of a primer for amplifying the analyte DNA molecules. Product beads are formed which are bound to a plurality of copies of one species of analyte DNA molecule. The product beads are separated from analyte DNA molecules which are not bound to product beads. Product beads which are bound to a plurality of copies of a first species of analyte DNA molecule are isolated from product beads which are bound to a plurality of copies of a second species of analyte DNA molecule.

Another aspect of the invention is an improvement of a method for analyzing nucleotide sequence variations in which microemulsions comprising one or more species of analyte DNA molecules are formed, the analyte DNA molecules in the microemulsions are amplified in the presence of reagent beads, wherein the reagent beads are bound to a plurality of molecules of a primer for amplifying the analyte DNA molecules, product beads are formed which are bound to a plurality of copies of one species of analyte DNA molecule, the product beads are separated from analyte DNA molecules which are not bound to product beads, and a sequence feature of the one species of analyte DNA molecule which is bound to the product beads is determined. The improvement is the use of a tissue mixer mill disrupter to form a plurality of separate microemulsion populations simultaneously in a multi-well plate using and a metal ball in each well.

These and other embodiments which will be apparent to those of skill in the art upon reading the specification provide the art with tools for more efficiently analyzing DNA variations.

BRIEF DESCRIPTION OF THE DRAWINGS

FIGS. 3A-3B show an analysis of bead populations with flow cytometry. Circled population in FIG. 3A (single beads) is shown in FIG. 3B, representing beads labeled with a sequence-specific FITC signal.

DETAILED DESCRIPTION OF THE INVENTION

Figure 1:
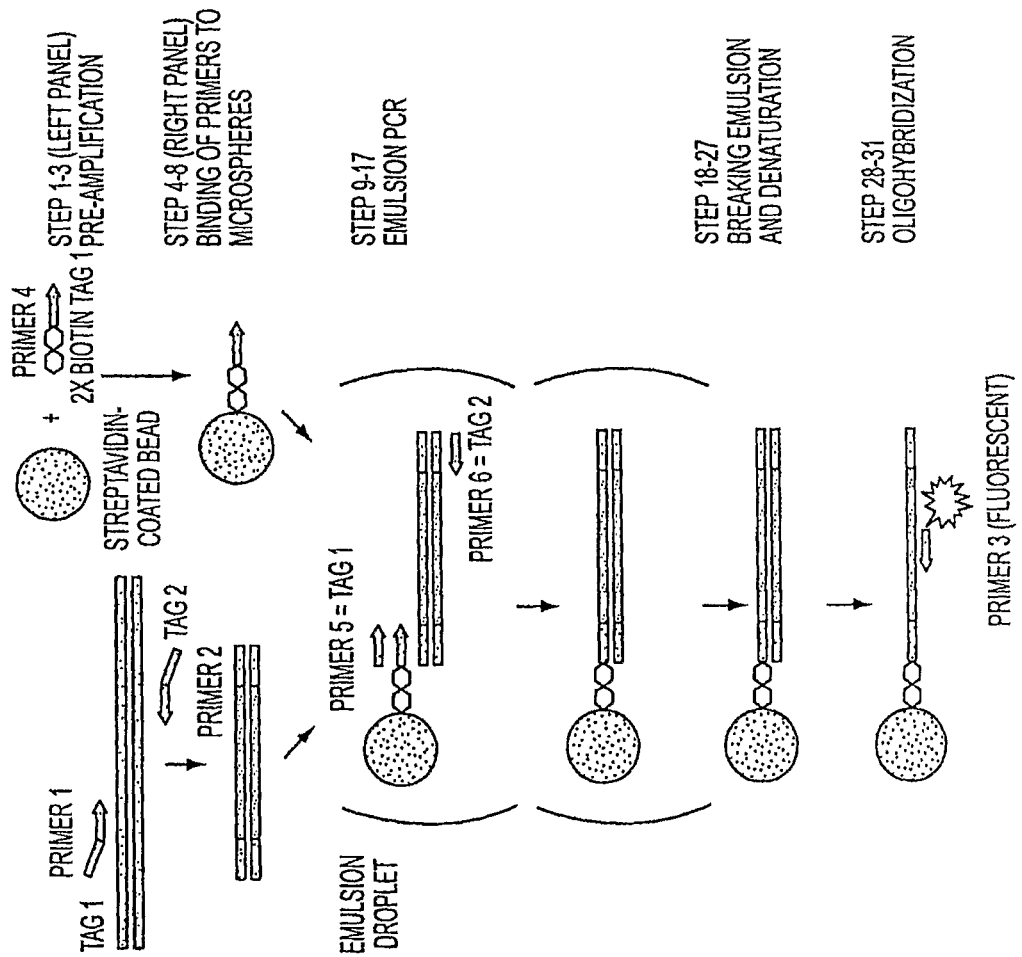
FIG. 1 diagrams the BEAMing procedure. References to the steps in the protocol are indicated along with each key step.

The inventors have developed methods which improve on former methods for practicing BEAMing. The methods described below provide for more homogenous populations of beads that have a higher amount of DNA on each bead at the end of cycling. Moreover, the use of the tissue lyser and metal beads to make a plurality of microemulsions in parallel massively increase throughput from single or double parallel samples to hundreds of parallel samples.

The aqueous phase in the microemulsions typically comprises at least 10, 15, 20, or 25, and up to 30% (v/v) of the microemulsions. The oil phase typically comprises at least 70, 75, 80, or 85, and up to 90% (v/v) of microemulsions. The emulsifier, although amphiphilic, is considered part of the oil phase. It is believed to align at the interface of the two phases upon formation of an emulsion. Hydrocarbons which form the oil phase are typically oils or waxes. These are characterized by their viscosities as shown below:

| | |
|---|---|
| Very low | <5 mPas at 25° C. |
| Low | 5-10 mPas at 25° C. |
| Medium | 10-20 mPas at 25° C. |
| High | 20-50 mPas at 25° C. |
| Very high | >50 mPas at 25° C. |

A lower viscosity oil (defined as a very low, low, and/or medium) is easier to work with than a high viscosity oil. The low viscosity oil can have a viscosity of less than 10 or less than 5 mPas at 25° C. However, mixing a small amount of the higher viscosity oil into the oil phase provides increased uniformity among product beads and higher amplification levels. The high viscosity oil can be within a range of 10-30, 20-25, or 22-26 mPas at 25° C. The majority of the oil phase can be either a very low, a low, a medium, or a mixture of such oils or waxes. The proportion of lower viscosity oil to high viscosity oil can vary from 85:10 to 60:30. At least 60, 65, 70, 75, or 80 and up to 85% (v/v) of the oil phase can be a lower viscosity oil. At least 10, 15, 17, 20, or 25, and up to 23, 25, 27, or 30% (v/v) of the oil phase can be a high viscosity oil. The emulsifier can comprise at least 5, 6, 7, 8, or 9% and up to 10% (v/v) of the oil phase.

After amplification, product beads can be analyzed to determine a sequence feature of the DNA bound to them. Any method for determining a sequence feature can be used, including, hybridization, primer extension, and nucleotide sequencing. Alternatively, product beads can be analyzed by FACs analysis, i.e., a technique for separating or distinguishing two different species of nucleotide molecule. Other means of analysis can be used as is convenient.

Beads according to the present invention are also known as microspheres or microparticles. Particle sizes can vary between about 0.1 and 10 microns in diameter. Typically beads are made of a polymeric material, such as polystyrene, although nonpolymeric materials such as silica can also be used. Other materials which can be used include styrene copolymers, methyl methacrylate, functionalized polystyrene, glass, silicon, and carboxylate. Optionally the particles are superparamagnetic, which facilitates their purification after being used in reactions.

Beads can be modified by covalent or non-covalent interactions with other materials, either to alter gross surface properties, such as hydrophobicity or hydrophilicity, or to attach molecules that impart binding specificity. Such molecules include without limitation, antibodies, ligands, members of a specific-binding protein pair, receptors, nucleic acids. Specific-binding protein pairs include avidin-biotin, streptavidin-biotin, and Factor VII-Tissue Factor.

Beads, after being prepared according to the present invention as product beads, have more than one copy of the same nucleic acid molecule bound to them. Preferably each bead is bound to at least 10, 50, 100, 500, or 1000 molecules of the same nucleic acid sequence. In some circumstances some of the product beads are bound to more than one type of nucleic acid molecule. These product beads are generally less useful in the analysis of ratios of genetic sequences in a population of genetic sequences. Such product beads can be readily discriminated and so will not distort the analysis.

A population of product beads will often comprise two or more types of nucleic acids. Such a population is heterogeneous with respect to the nucleic acids. Desirably, a substantial proportion of the product beads comprise only one type of nucleic acid per bead. A substantial proportion can be for example, at least 1%, at least 5%, at least 10%, or at least 50%. A product bead with only one type of nucleic acid per bead is termed homogeneous. Homogeneous beads with only one type of nucleic acid per bead include those with nucleic acids containing errors due to errors in polymerase chain reaction. A product bead with two types of nucleic acid per bead is termed heterogeneous. Although not wishing to be bound by any particular theory, heterogeneous product beads are thought to result from aqueous compartments which have more than two molecules of template of non-identical sequence. A population of product beads can be heterogeneous as a population but contain individual product beads that are homogeneous Individual product beads preferably comprise more than one copy of template analyte molecule. Each bead may comprise at least 10, at least 50, at least 100, at least 500, or at least 1000 copies of template analyte. If the bead is homogeneous, each of those copies will be identical.

Populations of product beads can be maintained in a liquid suspension. Alternatively they can be sedimented and dried or frozen. The latter alternatives may be beneficial for storage stability.

Analysis of populations of product beads can be useful for distinguishing between many kinds of genetic variants. Polynucleotides can be distinguished which differ by as little as a single nucleotide polymorphism (SNP), by the presence or absence of a mutation, by the presence or absence of an insertion or deletion, by the presence or absence of a nonsingle nucleotide polymorphism. Thus populations of product beads may be heterogeneous with regard to these genetic variations.

One very convenient way for distinguishing genetic variants, i.e., determining a sequence feature of the analyte, is by differentially labeling the variants with fluorescent dyes. Such labeling can be accomplished by hybridization of a fluorescently labeled oligonucleotide probe to one species of polynucleotide. Alternatively, a fluorescently labeled antibody can be used to specifically attach to one oligonucleotide probe that hybridizes to a particular genetic variant. Such antibody binding can be, for example, mediated by a protein or polypeptide which is attached to an oligonucleotide hybridization probe. Of course, other means of labeling polynucleotides as are known in the art can be used without limitation. Another means of labeling different polynucleotide species is by primer extension. Primers can be extended using labeled deoxyribonucleotides, such as fluorescently labeled deoxyribonucleotides.

Populations of product beads can be used as templates. Template analyte molecules on the product beads can be analyzed to assess DNA sequence variations by hybridization, primer-extension methods, mass spectroscopy, and other methods commonly used in the art. Template analyte molecules on product beads can be employed for solid phase sequencing. In one solid phase sequencing technique, product beads are arrayed by placing them on slides spotted with complementary oligonucleotides. In another solid phase sequencing technique, product beads are placed into individual wells. In still another solid phase sequencing technique product beads are incorporated into acrylamide matrices (with or without subsequent polony formation). Sequencing reactions can be performed with any solid phase sequencing method, such as those using unlabeled nucleotide precursors (e.g., pyrosequencing, as described in Ronaghi et al., *Anal. Biochem.* 267: 65-71, 1999) or labeled nucleotides (e.g., photocleavable reagents described by Mitra et al., *Anal. Biochem.* 320:55-65, 2003). Product beads can thus be used for and facilitate multiple parallel sequencing. Product beads can also be used in sequencing employing Type IIS restriction endonucleases. Product beads can also be used to provide templates for conventional dideoxynucleotide sequencing. To obtain useful data upon sequence analysis, a homogeneous template population is desirable. To provide a homogenous template population, product beads can be diluted, separated, or otherwise isolated so that each sequencing reaction contains a single product bead. Alternatively, product beads can be sorted to provide populations of beads with a single species of template.

Oligonucleotide primers can be bound to beads by any means known in the art. They can be bound covalently or non-covalently. They can be bound via an intermediary, such as via a protein-protein interaction, such as an antibody-antigen interaction or a biotin-avidin interaction. Other specific binding pairs as are known in the art can be used as well. To achieve optimum amplification, primers bound to the bead may be longer than necessary in a homogeneous, liquid phase reaction. Oligonucleotide primers may be at least 12, at least 15, at least 18, at least 25, at least 35, or at least 45 nucleotides in length. The length of the oligonucleotide primers which are bound to the beads need not be identical to that of the primers that are in the liquid phase. Primers can be used in any type of amplification reaction known in the art, including without limitation, polymerase chain reaction, isothermal amplification, rolling circle amplification, self-sustaining sequence replication (3SR), nucleic acid sequence-based amplification (NASBA), transcription-mediated amplification (TMA), strand-displacement amplification (SDA), and ligase chain reaction (LCR).

Microemulsions are made by stirring or agitation of oil, aqueous phase, and detergent. The microemulsions form small aqueous compartments which have an average diameter of 0.5 to 50 microns. The compartments may be from 1 to 10 microns, inclusive, from 11 to 100 microns, inclusive, or about 5 microns, on average. All such compartments need not comprise a bead. Desirably, at least one in 10,000 of said aqueous compartments comprise a bead. Typically from 1/100 to 1/1 or from 1/50 to 1/1 of said aqueous compartments comprise a bead. In order to maximize the proportion of beads which are homogeneous with respect to oligonucleotide, it is desirable that on average, each aqueous compartment contains less than 1 template molecule. Aqueous compartments will also desirably contain whatever reagents and enzymes are necessary to carry out amplification. For example, for polymerase chain reaction (PCR) the compartments will desirably contain a DNA polymerase and deoxyribonucleotides. For rolling circle amplification a DNA polymerase and a generic DNA circle may be present.

Emulsions can be "broken" or disrupted by any means known in the art. One particularly simple way to break the emulsions is to add more detergent. Detergents which can be used include, but are not limited to Triton X100, Laureth 4, Nonidet.

Sample DNA for amplification and analysis according to the present invention can be genomic DNA, cDNA, PCR products of genomic DNA, or PCR products of cDNA, for example. Samples can be derived from a single individual, for example, from a body sample such as urine, blood, sputum, stool, tissue or saliva. Samples can also be derived from a population of individuals. The individuals can be humans, but can be any organism, plant or animal, eukaryotic or prokaryotic, viral or non-viral.

Any type of probe can be used for specific hybridization to the amplified polynucleotides which are bound to the beads. Fluorescently labeled probes are useful because their analysis can be automated and can achieve high throughput. Fluorescence activated cell sorting (FACS) permits both the analysis and the isolation of different populations of beads. One type of fluorescently labeled probe that can be used is a modified molecular beacon probe. These probes have stem-loop structures and an attached fluorescent moiety on the probe, typically on one end of the probe, sometimes attached through a linker. Unlike standard molecular beacon probes, modified molecular beacon probes do not have a quenching moiety. The modified molecular beacon probe can have the fluorescent moiety attached on either end of the probe, 5' or 3'. One such probe will hybridize better to a wild-type sequence than to a mutant. Another such probe will hybridize better to a mutant sequence than to the wild type. Still other probes will preferably hybridize to one polymorphic variant over another.

High fidelity DNA polymerases which can be used are those which provide a higher rate of fidelity (lower rate of errors) than Taq polymerase. Preferably these provide an error rate of less than $10^{-5}$, more preferably an error rate of less than $5 \times 10^{-6}$, and even more preferably an error rate of less than $10^{-6}$. Suitable polymerases include: Phusion™ DNA polymerase (NEB), Taq High Fidelity™, and PfuUltra™. These are used in a thermal cycling polymerase chain reaction, as is conventional in the art.

Microemulsions are formed with beads and primers as previously taught. Because BEAMing requires thermal cycling, an emulsifier which is thermostable can be used. One such emulsifier is Abil® EM90 (Degussa-Goldschmidt Chemical, Hopewell, Va.). Other such emulsifiers can be used as are known in the art. Increased molecular weight of emulsifiers correlates with increased thermostability.

Amplicons can be any size which is efficiently amplified using polymerase chain reaction. In the case of templates obtained from serum of cancer patients, amplicons are preferably shorter than or equal to 300 bp, or shorter than or equal to 200 bp, or shorter than or equal to 100 bp. Templates from serum of colon cancer patients are apparently degraded to small sizes. Thus amplification of a smaller amplicon results in a more efficient and sensitive detection. The dependence of detection on size is quite strong as shown in FIG. 1.

Single base extension reaction with differentially labeled dideoxynucleotides provides a sensitive means for detecting sequence features. If upon detection of products, individual beads are found with multiple, distinct labels, for example, representing a mutant and a wild type nucleotide, they can be discarded from further analysis. Multiple, distinct labels in this context indicates that a bead was present in a microemulsion with two distinct templates of analyte DNA, rather than the desired single template, or that an error occurred early in an amplification reaction in a microemulsion, such that the erroneous and the correct templates were both amplified.

One means for detecting a sequence feature on an amplicon bound to a bead employs a single base extension (SBE) reaction. This reaction typically employs labeled dideoxynucleotide triphosphates to ensure that only a single monomer addition occurs. Dideoxynucleotide triphosphates can be conveniently labeled with any type of detectable label, including radioactive, fluorescent, and luminescent moieties. Different labels can be attached to different dideoxynucleotide triphosphates (ddNTPs) so that different products can be detected in the same sample. Prior to addition of all reagents necessary for initiation of the SBE reaction, unlabeled ddNTPs can be added to block non-specific extension. Typically at least one unlabeled ddNTP is added at a concentration five to 40 fold higher than the concentration of the labeled ddNTPs. Preferably the concentration is at least ten to twenty times higher. For example, if A is the mutant base and C is the wild-type base, during the SBE, we can use Rox-ddATP for the mutant, FITC-ddCTP for the wild type, ddGTP and ddTTP for blocking the nonspecific extension at the ratio of 1:2-10:20:20. The unlabeled ddNTPs reduce nonspecific incorporation.

Another optional step for improving the specificity and/or sensitivity of the SBE reaction is to denature the double stranded nucleic acid duplexes attached to the beads prior to the SBE reaction. For example, the double strands can be heated or treated with sodium hydroxide. After the separation of the two strands, the single strands which are not bound to the beads can be separated from the beads and the bead-bound strands, and the single strands can be discarded.

If desired, yet another step of amplification can be used after the microemulsions are broken. This step typically employs isothermal amplification, also known as rolling circle amplification. In order to generate the rolling circle, a molecular inversion probe or a padlock probe can be used. They probe may require filling-in, or not, prior to a template-driven ligation reaction to generate a circle. If filling-in is required the region to be filled in will typically be from 1 to 30 nucleotides. The isothermal amplification can amplify the ultimately detected signal quite significantly. After isothermal amplification, a sequence feature can be detected using SBE (single base extension) reaction, as described above. Alternatively, the nucleotide sequence of the amplicon on the beads can be determined by any sequencing method known in the art, including sequencing-by-synthesis.

Samples which may be used as sources of analyte DNA include blood, plasma, urine, stool, sputum, tears, saliva, and bone marrow. Solid tissues can also provide analyte DNA. Samples can be obtained from cancer patients, from related family members, from pregnant women, and from neonates. Sources of analyte DNA may be treated, for example with test agents, and the effects of the test agents on the analyte DNA can be determined.

While this protocol is an advancement of the current amplification methods, there are some limitations to the technology. One limitation is the size of the PCR products that can be polymerized on the beads. Though we have successfully amplified sequences as long as 2,700 bp via BEAMing, the yield of products of this large size is less than 5% of that achieved with amplicons <110 bp. Steric hindrance at the bead surface is probably responsible for the lower efficiency with long amplicons. This could conceivably be overcome in the future by using different beads with more enzyme-compatible surfaces or different polymerases (though no commercially available polymerases have so far been more efficient than the one described above).

Another limitation of the method is the need to prepare a different emulsion for each amplicon to be queried. This limitation has been overcome in part by the new emulsion-making procedure described herein, which can in principle be automated and allow simultaneous generation of 192 emulsions. It is possible that multi-parallel microfluidics could be used to generate greater numbers of emulsions, using processes such as those recently described'. Microfluidics also has the capacity to generate more homogeneous emulsions than methods based on shear force such as the one described herein.

There are other technologies that can achieve compartmentalized PCR using single molecules as templates. These include amplifications in the wells of picotiter plates[6] or in polonies[3]. These methods do not yield as many compartments as BEAMing but are adequate for several applications. BEAMing also offers the advantage that little special equipment, for either preparation of emulsions or their analysis, is required other than what is routinely available at most institutions.

Mastrobattista et al. have recently described a method to produce single template amplifications in water-oil-water (w/o/w) emulsions that can be directly used for flow cytometry[7]. Though the purposes for devising this method were distinct from the diagnostic applications driving the development of BEAMing, the droplets formed in the w/o/w-based procedure could be used for variant detection if a fluorescent probe, such as a Molecular Beacon, were incorporated into the aqueous phase. This would allow querying one or a few variations within an amplicon, while BEAMing allows query of any variant within an amplicon.

There have been several recent publications that described applications of BEAMing. In addition to its use as templates for high-throughput sequencing[3,8], it has been employed for the quantification of mutations in plasma samples of cancer patients[4], the direct determination of polymerase error rates and the identification of transcription factor targets[9].

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials

Reagents
Binding buffer: 5 mM Tris-HCl (pH 7.5), 0.5 mM EDTA, 1 M NaCl
Breaking buffer: 10 mM Tris-HCl (pH 7.5), 1% Triton-X100, 1% SDS, 100 mM NaCl, 1 mM EDTA
48-well cell culture plate (Corning, 3548)
Deoxynucleotide triphosphates (dNTPs) mix (10 mM each; USB, 77212)
FACS Sheath Solution (BD Biosciences, 342003)
5× hybridization buffer: 75 mM Tris-HCl (pH 9.5), 33.5 mM $MgCl_2$, 25% formamide Caution
Microamp clear adhesive film (Applied Biosystems, 4306311)
1.5 ml microcentrifuge tubes (Screw cap, Corning, 430909)
Mineral oil (Sigma, M3516)
MyOne streptavidin-coated magnetic beads, hydrophilic, 1-µm diameter (10 mg/ml; 7-12×10$^9$ beads/ml; Invitrogen, 650-01)
0.1 M NaOH Caution
10× PCR buffer: 670 mM Tris-HCl (pH 8.8), 166 mM $(NH_4)_2SO_4$, 100 mM (3-mercaptoethanol, 11.7 mM $MgCl_2$ Caution
Oil/emulsifier mix: 7% (w/v) ABIL WE09 in Tegosoft DEC (Degussa Goldschmidt Chemical; available from authors as it is only sold in amounts that are much larger than needed for laboratory experiments). Store mixture at room temperature for no longer than two days.
96-well PCR plates (Denville Scientific, C18096X)
Phusion/iProof high-fidelity DNA polymerase, (2 U/µl; NEB/Biorad, F-530L/172-5302)
Platinum Taq DNA polymerase (5 U/µl; Invitrogen, 10966-034)
Quant-iT PicoGreen dsDNA assay kit (Invitrogen, P-7589)
Stainless steel beads (5 mm; Qiagen, 69982)
96-well storage plates (1.2 ml; round well; round bottom; Abgene, AB-0564)
TE buffer: 10 mM Tris-HCl (pH 7.5), 1 mM EDTA
TK buffer: 20 mM Tris-HCl (pH 8.4), 50 mM KCl Oligonucleotides
Six oligonucleotide primers are required for a single BEAMing experiment, as illustrated in FIG. 1. Primers 1 to 3 are gene-specific while primers 4 to 6 are universal. We generally obtain oligonucleotides from IDT.

Primer3 (domain name:frodo.wi.mit.edu/cgi-bin/primer3, document: primer3_www.cgi) is used to design the gene-specific portions of the primers. These sequences should have a $T_m$ of ~60° C. and be 18 to 27 nucleotides in length.

Primers 1 and 2 are used for pre-amplification of the DNA template. Primer 1 contains a universal sequence (Tag 1, 5'-TCCCGCGAAATTAATACGAC-3'; SEQ ID NO: 1) on its 5'-end and a sequence homologous to the gene of interest at its 3' end. Primer 2 contains a second universal sequence (Tag 2, 5'-GCTGGAGCTCTGCAGCTA-3'; SEQ ID NO: 2) on its 5'-end and a sequence homologous to the gene of interest at its 3' end.

Primer 3 is used for detection of amplification products on beads and is labeled with a fluorescent group (e.g., FAM) at its 5' end.

Primer 4 is bound to the beads. It is doubly biotinylated at its 5' end and has a PEG 18 spacer and a thymidine base between the biotins and the Tag1 sequence, e.g., 5'-Dual biotin-Spacer18-T-TCCCGCGAAATTAATACGAC-3'; SEQ ID NO: 3.

Primers 5 and 6 are unmodified oligonucleotides with the Tag1 and Tag2 sequences, respectively.

The dual biotin group is essential to keep the oligonucleotide attached to the streptavidin-coated beads during thermal cycling[1].

Equipment
Centrifuge with swinging buckets for microtiter plates (4K15; Qiagen/Sigma)
Compression pads for a thermal cycler (Thermo Hybaid)
Flow cytometer (LSRII, BD Biosciences)
MPC-S and MPC-9600 magnetic separators (Invitrogen, 120-20D and 120-06D)
ND-1000 Spectrophotometer (NanoDrop Technologies)
TissueLyser mixer mill with adaptor plates from the 2× 24 adaptor set (Qiagen, 85210 and 69982)
Single-bead dispenser (Qiagen, 69965)

Example 2

Procedure

Note that all steps are performed at room temperature except where indicated otherwise.
Pre-Amplification of DNA Samples
1. Set up a 50 µl PCR reaction for the initial amplification of the target region, as follows:

| | |
|---|---|
| Primer 1 (10 µM) | 1 µl |
| Primer 2 (10 µM) | 1 µl |
| Template DNA (in water) | 15 µl |
| dNTPs mix | 1 µl |
| 5x Phusion HF buffer | 10 µl |
| Water | 21.5 µl |
| Phusion DNA polymerase (2 U/µl) | 0.5 µl |

Add the components in the order listed. Overlay PCR reaction with 15 µl mineral oil to prevent evaporation during the temperature cycling. Other DNA polymerases can also be used for this pre-amplification, depending on the fidelity required for the specific application[2].
If the template DNA is complex, such as mammalian cellular DNA, then we generally use 3 to 30 ng per PCR (1000-10,000 haploid genome equivalents).
2. Place the reaction in a thermal cycler and amplify the DNA fragment according to the following touchdown program:

| Cycle number | Denaturation | Annealing | Polymerization |
|---|---|---|---|
| 1 | 1 min at 98° C. | | |
| 2-4 | 10 s at 98° C. | 10 s at 70 s | 10 s at 72° C. |
| 5-7 | 10 s at 98° C. | 10 s at 67 s | 10 s at 72° C. |
| 8-10 | 10 s at 98° C. | 10 s at 64 s | 10 s at 72° C. |
| 11-40 | 10 s at 98° C. | 10 s at 61 s | 10 s at 72° C. |

It is possible to reduce the number of PCR cycles to minimize polymerase induced sequence errors. Touchdown PCR conditions minimize the formation of nonspecific amplification products but are not required.
3. Analyze the PCR product by agarose gel electrophoresis and quantify the DNA yield using the PicoGreen dsDNA kit.
The typical yield for a 120 bp amplicon is in the order of ~15 ng/µl (~200 nM). Excess primer from the pre-amplification competes with the primer on the beads and decreases the amount of PCR product bound to beads during the Emulsion PCR process. If the concentration of amplicon is less than 4 nM, then purify the PCR product with a QIAquick PCR purification kit to remove the PCR primers.
TROUBLESHOOTING
PAUSE POINT DNA can be stored at −20° C.
CRITICAL STEP
Binding of Primers to Beads 4. In a 1.5 ml microcentrifuge tube, wash 100 µl (7-12×10$^8$) streptavidin-coated magnetic beads twice with 100 µl TK buffer. After each wash, place the tube on a magnet for 1 min to concentrate the beads and remove the supernatant with a pipette.
This will result in enough beads to perform 18 emulsion PCRs.

5. Resuspend the beads in 100 µl Binding buffer and add 10 µl Primer 4 (100 µM, in TE buffer). Vortex immediately.

6. Incubate the bead suspension at 15-25° C. for 30 min. Every 10 minutes or so, mix the beads by briefly vortexing the tube.

7. Separate the beads, now coated with primers, with the magnet. Remove the supernatant and wash the beads 3 times with TK buffer as described above.

8. Resuspend the beads in 100 µl TK buffer.
PAUSE POINT Beads can be stored at 4° C. for at least 3 months.
CRITICAL STEP
Emulsion PCR 9. Prepare emulsifier/oil mix within one or two days of use. A precipitate in the Tegosoft DEC oil is occasionally observed in the bottom of the bottle; do not include this precipitate when preparing the mix.

10. Dilute the template DNA with TE to ~20 pM immediately prior to use.
DNA at low concentrations can stick to tubes during storage.

11. Set up a 150 µl amplification reaction by mixing the following:

| | |
|---|---|
| Primer 5 (2.5 µM) | 3 µl |
| Primer 6 (400 µM) | 3 µl |
| Template DNA (~20 pM) | 10 µl |
| Beads | 6 µl |
| dNTPs mix | 3 µl |
| 10x PCR buffer | 15 µl |
| Platinum Taq DNA polymerase (5 U/µl) | 9 µl |
| Water | 101 µl |

CRITICAL STEP

Figure 2:
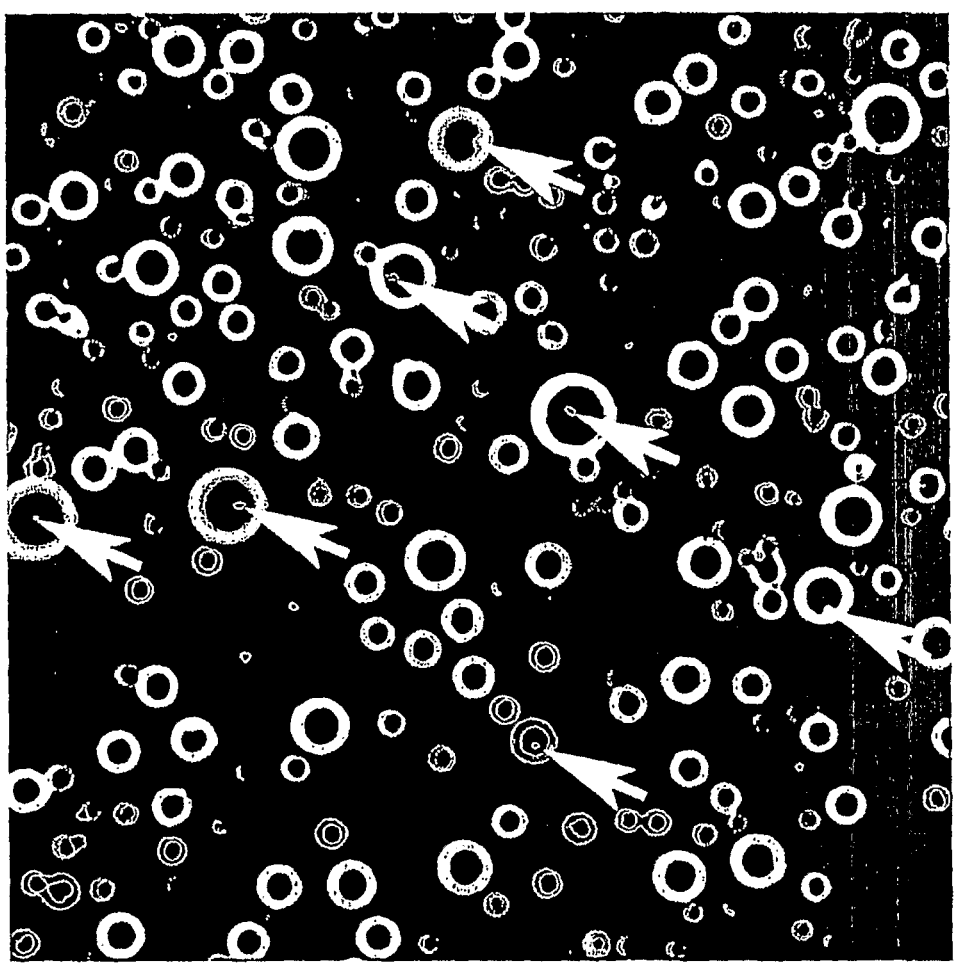
FIG. 2 shows a phase contrast micrograph at 400× of emulsions deposited in the well of a 48-well tissue culture plate. For reference, the beads (arrows) are 1.05 microns in diameter.

12. Add, in order, one steel bead, 600 µl oil/emulsifier mix, and 150 µl PCR reaction mix to one well of a 96-well storage plate. Seal plate with adhesive film.
The adhesive film will not seal properly, if oil is present on the rims of the wells. Turn the plate upside down to make sure the steel bead moves freely in the well.
CRITICAL STEP 13. Assemble a TissueLyser adaptor set by sandwiching the 96-well storage plate containing the emulsion PCR mix between the top and bottom adapter plates each fitted with a compression pad facing the 96-well storage plate. Place the assembly into the TissueLyser holder, and close the handles tightly. Mix for 10 s at 15 Hz and for 7 s at 17 Hz. Balance TissueLyser with a second adaptor set of the same weight.
CRITICAL STEP 14. Disassemble the adaptor set and centrifuge the plate for 10 sec at ~3 g to get the liquid to the bottom 15. Assess the quality of the emulsions at 400× magnification with an inverted microscope.
Take a pipette tip, dip it into the emulsion, and streak it over the bottom of a 48-well cell culture plate. Do not use coverslips, as these can alter the quality of the emulsion.
Examine sample immediately as the aqueous compartment evaporates quickly. FIG. 2 shows a photograph of emulsions prepared by this process.
TROUBLESHOOTING 16. Aliquot 80 µl of the emulsion into eight wells of a 96-well PCR plate.
Pipette emulsions slowly to avoid shear force. Centrifuge the plate for 10 sec at ~3 g to get the liquid to the bottom.

17. Temperature cycle the emulsions according to the following program:

| Cycle number | Denaturation | Annealing | Polymerization |
|---|---|---|---|
| 1 | 2 min at 94° C. | | |
| 2-4 | 15 s at 98° C. | 45 s at 64 s | 75 s at 72° C. |
| 5-7 | 15 s at 98° C. | 45 s at 61 s | 75 s at 72° C. |
| 8-10 | 15 s at 98° C. | 45 s at 58 s | 75 s at 72° C. |
| 11-60 | 15 s at 98° C. | 45 s at 57 s | 75 s at 72° C. |

PAUSE POINT Emulsions can be stored at 4° C.
Breaking Emulsions

18. To each 80 µl emulsion, add 150 µl Breaking buffer and pipette up and down 3 times to mix.

19. Seal the PCR plate, place it into an empty 96-well storage plate, and assemble between two TissueLyser adaptor plates as described above (Step 13). Place in TissueLyser and mix for 30 s at 20 Hz.

20. Remove PCR plate from the TissueLyser and centrifuge for 2 min at 3200 g.

21. Remove the top oil layer with a 20 µl pipette tip attached to a vacuum manifold.

22. Add 150 µl Breaking buffer, seal the plate, and centrifuge again for 2 min at 3200 g.

23. Place the plate in a 96-well magnetic separator for 1 min and completely remove the liquid with a pipette.

24. Remove the plate from the magnet, resuspend the beads in 100 µl TK buffer, and pool the beads from the eight wells into a 1.5 ml tube.

25. Place the tube on the magnet to concentrate the beads for 1 min and carefully remove the supernatent with a pipette.
TROUBLESHOOTING 26. Resuspend beads in 500 µl of 0.1 M NaOH and incubate for 2 min. Place the tube in magnetic separator for 1 min and carefully remove supernatant.
This removes the non-biotinylated DNA strand from the beads.

27. Resuspend the beads in 100 µl TK buffer.
The recovery of beads can be assessed by measuring absorption at 600 nm. The Nanodrop spectrophotometer is convenient for this purpose as it only requires 2 µl bead suspension. An aliquot of the beads coated with Primer 5 can be used as a fiducial. The typical recovery with the procedure described above is 50-70%.
TROUBLESHOOTING
PAUSE POINT Beads can be stored at 4° C.
Detection of DNA on the Beads 28. Set up the oligohybridization in a 96-well PCR plate by mixing the following:

| | |
|---|---|
| Primer 3 (1 μM) | 10 μl |
| Beads | 20 μl |
| 5x hybridization buffer | 20 μl |
| Water | 60 μl |

The number of beads to be used depends on the nature of the experiment. Ten million beads provide a great enough mass to be seen during magnetic collection and facilitate recovery. The recovery can be assessed by measuring absorption at 600 nm as described above.
29. Incubate at 50° C. for 15 min in a thermal cycler.
30. Place the plate on a 96-well magnetic separator for 1 min to concentrate the beads and remove 80 μl of the supernatant with a pipette.
31. Wash beads twice with 80 μl TK buffer.
PAUSE POINT Beads can be stored at 4° C.
Analysis of Bead Populations
32. Use flow cytometry to determine the relative fluorescence intensity of the primers hybridized to the DNA on the beads.
We have successfully used the BD Bioscience FACScan, LSR I & II, FACSCalibur, and FACSAria. Alternatively, fluorescence microscopy can provide a rapid qualitative analysis of the beads generated.
CRITICAL STEP*
33. Empirically, establish the amplifier gain (voltages) for the detection of the forward scatter (FCS), side scatter (SSC), and fluorescence signal.
FIG. 3 illustrates typical results obtained.
TROUBLESHOOTING**
CRITICAL STEP*
Critical Steps
Critical Step 3
The amount of DNA used in the emulsion PCR can be varied over a relatively wide range. Optimally, 20%+/−15% of the beads should contain PCR products. Too little template results in too few positive beads, compromising the sensitivity of analysis. Too much template results in too many compartments containing multiple templates, making it difficult to accurately quantify the fraction of initial templates containing the sequence of interest.
Critical Step 8
Many beads in addition to the 1.05 micron MyOne beads can be used for this procedure. MyOne beads are uniform, which is especially advantageous for flow cytometry. Other magnetic beads (such as Sera-Mag particles from Seradyn) have more surface streptavidin molecules than MyOne and can be used when surface density is more important than uniformity. Larger uniform beads (such as Dynabeads M-280) have even more surface streptavidin molecules, but are much more expensive (per bead) and the emulsion formulation must be altered to make the them efficient supports. Finally, non-magnetic beads can be used, though these are more difficult to handle because centrifugation rather than magnets must be used to manipulate them.
Critical Step 11
The efficiency of amplification on solid supports in emulsions decreases with increasing amplicon length[3]. The preferred amplicon length (including primers) is 70 to 110 bp. Amplicons of 200 bp yield ~30% of the product of those containing 100 bp on beads. We generally use a universal primer (Primer 5 in FIG. 1) as the reverse primer. However, one can also use a nested reverse primer that results in an amplicon shorter than the product of the pre-amplification step to reduce nonspecific amplification on the microspheres or to decrease the size of the bead-bound PCR product and thereby increase yield. Finally, the concentration and type of polymerase has been extensively optimized in the protocol described here. In general, higher polymerase concentrations result in higher yields of PCR products bound to beads. Another way to increase the amount of PCR product bound to the beads is through rolling circle polymerization[2].
Critical Step 12
If a TissueLyser is not available, emulsions can also be generated using a stir-bar or a homogenizer[1,4]. Though the emulsions are not as uniform or as easily controlled as those made with the TissueLyser, they are adequate for many applications of BEAMing, especially when only a small number of samples is required. One simple way to prepare such emulsions is by mixing 240 μl PCR reaction with 960 μl 7% Abil EM90 in mineral oil (Sigma) in a 2 ml cryogenic vial (Corning, 430661) for 10 sec with a vortexer and for 50 sec with a homogenizer (IKA, T25 basic, 2953000) equipped with a disposable homogenizer tip (Omni Intl., 30750) at minimum speed[4].
Critical Step 13
When using the 96-well storage plate with the TissueLyser adaptor plates, samples closer to the body of the instrument (rows G and H) vibrate more slowly than samples in rows A and B. To prevent variation in emulsion quality, we recommend using only rows A and B if <24 samples are being prepared. When using the entire 96-well plate, rotate the to 96-well plate half way through the mixing process.
Critical Step 32
In the single tube operation mode of the FACSCalibur and LSR I & II instruments, the droplet containment module (DCM) sleeve above the sample injection tube (SIT) should be removed to prevent the 1 micron magnetic beads from getting trapped between the sleeves. The sleeve can be replaced by a shorter modified metal sleeve protector. We also recommend using high quality sheath fluid.
Critical Step 33
The forward scatter resolution of instruments using a traditional photodiode detector should be sufficiently sensitive to detect single 1 micron particles. However, if not properly aligned the beads will be difficult to separate from background. A forward scatter photomultiplier tube (PMT) detection system increases sensitivity down to a resolution of 0.2 μm and is recommended when using beads of 1 micron in diameter.
Troubleshooting Table
Problem Step 3 Desired Band is not the Dominant Product of the Pre-Amplification.
Solution
Use a higher annealing temperature (60 to 65° C.) and vary the $MgCl_2$ concentration (1.5 mM to 2.5 mM). GC-rich templates should be amplified in Phusion GC buffer and 3-6% DMSO. Check that the sequence is not repeated in the template genome. Check for homodimer and heterodimer formation with an oligo analyzer program (e.g. Oligonucleotide Properties Calculator; http://www.basic.northwesternedu/biotools/oligocalc.html). It is worth trying several primer pairs if amplification is a problem.
Problem Step 15 Aqueous Droplets are Too Small or Too Big.
Solution
If the aqueous compartments of an emulsion are too small there will be little or no amplification. If the compartments are too large, the fraction of compartments with only a single template will be too low to provide a statistically significant result. The droplet sizes can be optimized varying the mixing time or vibration speed by increments of 1 s or 1 Hz, respectively.

Problem Step 25 Beads Form Visible Aggregates.

Solution

We have occasionally observed aggregates of magnetic beads at various steps after breaking the emulsions. This occurs more frequently with larger amplicons (>200 bp). The factors that might be responsible are the time a sample is placed in the magnetic field, the salt concentration and the temperature of the buffers. In order to minimize the likelihood of aggregate formation use only buffers equilibrated at room temperature. The samples should not be left on the magnet for more than 2 min (especially after the liquid has been removed). The salt concentration can be increased. Once aggregates have formed they are hard to disperse. In some cases they can be dispersed by pipetting, vortexing, or sonicating (Bioruptor from Diagenode). Heating also can help reverse aggregation in some cases.

Problem Step 27 Low Recovery of Beads after Emulsion PCR.

Solution

Low recoveries can result from incomplete demulsification or inefficient magnetic separation. To prevent incomplete demulsification increase the mixing time and speed. To prevent loosing beads during the magnet separation never remove all of the supernatant, do not touch the bead pellet, and use the same brand of tubes, plates and magnets as suggested above.

Problem Step 33 Poor Signal to Noise.

Solution

This is usually due to a low efficiency of on-bead amplification but can be due to substandard hybridization conditions or to a poor probe (e.g. secondary structure preventing hybridization). Purification of hybridization probes by HPLC or gel electrophoresis is recommended. Check the hybridization conditions by hybridizing a primer to the beads that is complementary to Tag1. The signal obtained represents the maximal signal possible, as every PCR product on the bead has this sequence at its 5' end. The signal from these beads should be equivalent to those achieved by binding a 5'-biotinylated oligonucleotide that has a similar fluorescent group on the 3' end. The signal from Primer 3 should be within 10-fold of the signal obtained with Tag1, meaning that at least 10% of the bead-bound primers were extended during the PCR. Low amounts of DNA on the beads can be caused by a small size of the aqueous compartments (see Problem Step 15), or poor reaction conditions. Note that extensive optimization has been performed on every aspect of the protocol described herein and deviations from these conditions should be undertaken with caution.

REFERENCES

The disclosure of each reference cited is expressly incorporated herein.

1. Dressman, D., Yan, H., Traverso, G., Kinzler, K. W. & Vogelstein, B. Transforming single DNA molecules into fluorescent magnetic particles for detection and enumeration of genetic variations. *Proc Natl Acad Sci USA* 100, 8817-8822 (2003).
2. Li, M., Diehl, F., Dressman, D., Vogelstein, B. & Kinzler, K. W. BEAMing up for detection and quantification of rare sequence variants. *Nat Methods* 3, 95-97 (2006).
3. Shendure, J. et al. Accurate multiplex polony sequencing of an evolved bacterial genome. *Science* 309, 1728-1732 (2005).
4. Diehl, F. et al. Detection and quantification of mutations in the plasma of patients with colorectal tumors. *Proc Natl Acad Sci USA* (2005).
5. Utada, A. S. et al. Monodisperse double emulsions generated from a microcapillary device. *Science* 308, 537-541 (2005).
6. Nagai, H., Murakami, Y., Morita, Y., Yokoyama, K. & Tamiya, E. Development of a microchamber array for picoliter PCR. *Anal Chem* 73, 1043-1047 (2001).
7. Mastrobattista, E. et al. High-throughput screening of enzyme libraries: in vitro evolution of a beta-galactosidase by fluorescence-activated sorting of double emulsions. *Chem Biol* 12, 1291-1300 (2005).
8. Margulies, M. et al. Genome sequencing in microfabricated high-density picoliter reactors. *Nature* 437, 376-380 (2005).
9. Kojima, T. et al. PCR amplification from single DNA molecules on magnetic beads in emulsion: application for high-throughput screening of transcription factor targets. *Nucleic Acids Res* 33, e150 (2005).

The invention claimed is:

1. A liquid composition comprising a plurality of microemulsions forming aqueous compartments wherein at least a portion of said aqueous compartments comprise:
 a bead;
 a polynucleotide template; and
 oligonucleotide primers for amplifying said template;
 wherein at least a portion of the oligonucleotide primers is bound to the bead, wherein said microemulsions comprise an oil phase and an aqueous phase, wherein the aqueous phase comprises from 10-30% (v/v) of the microemulsions and the oil phase comprises from 70-90% (v/v) of the microemulsions; wherein the oil phase comprises one or more low viscosity hydrocarbons with a viscosity less than 20 mPas at 25° C. in an amount from 60-85% (v/v) of the oil phase, one or more high viscosity hydrocarbons having a viscosity of greater than 20 mPas at 25° C. in an amount from 10-30% (v/v), and an emulsifier in an amount from 5-10% (v/v).

2. The liquid composition of claim 1 wherein the microemulsions comprise the high viscosity hydrocarbons in an amount from 15-25% (v/v) of the oil phase.

3. The liquid composition of claim 1 wherein the microemulsions comprise the high viscosity hydrocarbons in an amount from 17-23% (v/v) of the oil phase.

4. The liquid composition of claim 1 wherein a plurality of separate microemulsion populations are formed simultaneously in a multi-well plate using a tissue mixer mill disruptor and a metal ball in each well.

5. The liquid composition of claim 1 wherein the low viscosity hydrocarbons comprise an oxygen moiety selected from the group consisting of: a hydroxyl, an ester, an ether, and a carboxylic acid.

6. The liquid composition of claim 1 wherein the high viscosity hydrocarbons have a viscosity of 20-30 mPas at 25° C.

7. The liquid composition of claim 1 wherein the high viscosity hydrocarbons have a viscosity of 20-25 mPas at 25° C.

8. The liquid composition of claim 1 wherein the high viscosity hydrocarbons have a viscosity of 22-26 mPas at 25° C.

9. The liquid composition of claim 1 wherein the low viscosity hydrocarbons are selected from the group consisting of: 4-glyceryl isostearate, ethylene glycol, propylene glycol, cetyl propylene glycol, hexyl laurate, diethyl hexylcarbonate, and mixtures thereof.

10. The liquid composition of claim 1 wherein the low viscosity hydrocarbons have a viscosity of less than 15 mPas at 25° C.

11. The liquid composition of claim 1 wherein the low viscosity hydrocarbons have a viscosity of less than 10 mPas at 25° C.

12. The liquid composition of claim 1 wherein the low viscosity hydrocarbons have a viscosity of less than 5 mPas at 25° C.

* * * * *